United States Patent [19]
Jagpal

[11] Patent Number: 5,257,979
[45] Date of Patent: Nov. 2, 1993

[54] INSTRUMENT FOR CATHETERIZATION

[76] Inventor: Ravindar Jagpal, 7301 Parkshire Ave., Dallas, Tex. 75231

[21] Appl. No.: 919,912

[22] Filed: Jul. 27, 1992

[51] Int. Cl.⁵ .............................................. A61M 5/32
[52] U.S. Cl. ..................................... 604/272; 604/104
[58] Field of Search ............... 604/164, 171, 264, 272, 604/162, 104

[56] References Cited

U.S. PATENT DOCUMENTS

| | | | |
|---|---|---|---|
| 4,192,302 | 3/1980 | Boddie | 128/214 R |
| 4,280,503 | 7/1981 | Ackerman | 128/419 P |
| 4,327,723 | 5/1982 | Frankhauser | 128/214.4 |
| 4,515,593 | 5/1985 | Norton | 604/265 |
| 4,525,157 | 6/1985 | Vaillancourt | 604/52 |
| 4,540,404 | 9/1985 | Wolvek | 604/96 |
| 4,652,256 | 3/1987 | Vaillancourt | 604/52 |
| 4,654,031 | 3/1987 | Lentz | 604/272 |
| 4,655,750 | 4/1987 | Vaillancourt | 604/165 |
| 4,763,671 | 8/1988 | Goffinet | 128/786 |
| 4,781,676 | 11/1988 | Schweighardt et al. | 604/21 |
| 4,844,092 | 7/1989 | Rydell et al. | 128/772 |
| 4,898,583 | 2/1990 | Borsanyl et al. | 604/153 |
| 4,935,008 | 6/1990 | Lewis, Jr. | 604/52 |
| 4,993,707 | 1/1985 | Ishihara | 604/272 |
| 4,995,866 | 2/1991 | Amplatz et al. | 604/83 |
| 5,011,478 | 4/1991 | Cope | 604/264 |
| 5,069,662 | 12/1991 | Bodden | 604/4 |
| 5,205,829 | 4/1993 | Litochy | 604/264 |

OTHER PUBLICATIONS

"Fabrication and Clinical Application of Intrahepatic Arterial Catheter Facilitating Repeated Infusion Therapy and Experience", Y Une et al., *Gan To Kagaku Ryoho* (Japan) Aug. 1988 (8 Pt 2) pp. 2379–2383.

"Efficacy of an Attachable Subcutaneous Cuff for the Prevention of Intravascular Catheter-Related Infection", R. H. Flowers, III, et al., *JAMA*, Feb. 10, 1989, vol. 261, No. 6, pp. 878–883.

"An Overview of Interstitial Brachytherapy and Hyperthermia", Beverly B. Brandt and James Harney, *Oncology Nursing Forum*, vol. 16, No. 6, pp. 833–841, 1989.

"Catheter-Related Sepsis: Prospective, Randomized Study of Three Methods of Long-Term Catheter Maintenance", Steven Eyer, M.D., et al., *Critical Care Medicine*, vol. 18, No. 10, pp. 1073–1079 Oct. 1990.

"Central Venous Catheter Related Sepsis: A Clinical Review", Chaim Putterman, *Resuscitation*, 20 (1990), 1–16.

"Clinical Predictors of Infection of Central Venous Catheters Used for Total Parenteral Nutrition", Carl W. Armstrong, M.D., et al., *Infect Control Hosp Epidemiol* 1990, vol. 11, No. 2, pp. 71–78.

"Preventing Central Venous Catheter-Related Complications", Thomas R. Beam, Jr., M.D., et al., *Infections in Surgery*, Oct. 1990, pp. 1–13.

(List continued on next page.)

*Primary Examiner*—Paul J. Hirsch
*Attorney, Agent, or Firm*—Ross, Howison, Clapp & Korn

[57] ABSTRACT

A system and method of catheterization includes a needle, a "Y" connector, a syringe, a dilator, a sheath, a protective sleeve and a shock sheath. This introduces a comprehensive, uniform and universal approach to catheterization. Discriminatory methods of treatment using the invention are described. Particular attention has been paid to current problems in catheterization and the prevention of transmission of communicable diseases from patient to practitioner and vice-versa (e.g., the risk of contracting the HIV virus is substantially reduced using this system and method). The invention makes possible substantial decreases in the cost of health care while improving the efficiency of diagnosis and treatment. It allows the practitioner to perform simultaneous diagnosis and treatment of diseases using the same procedure, regardless of their location in or on the body. The number and duration of hospitalization is minimized, and the quality of life and length of survival for the patient are improved.

39 Claims, 4 Drawing Sheets

OTHER PUBLICATIONS

"The Pathogenesis and Epidemiology of Catheter-Related Infection With Pumonary Artery Swan--Ganz Catheters: A Prospective Study Utilizing Molecular Subtyping", Leonard A. Mermel, D.O., Sc.M., et al., *The American Journal of Medicine*, vol. 91 (suppl 3B), Sep. 16, 1991, pp. 197s–205s.

"Arrow-Howes Multi-Lumen Catheter With Antiseptic Surface and VitaCuff", *Arrow International Technical Report*, 1990.

"Air Emboli: A Potentially Lethal Complication of Central Venous Lines", Jackie Bretz Thielen, R.N., M.S.N., C.C.R.N., *Focus on Critical Care.AACN*, vol. 17, No. 5, Oct. 1990, pp. 374, 378–380, 382–383.

"Central Venous Air Embolism Without a Catheter", Karl A. Poterak, M.D., Anil Aggarwal, M.D., *Canadian Journal of Anaesthesia* 1991, vol. 38:3, pp. 338–340, Apr. 1991.

"Late Radiation Damage in Normal Tissue", Elizabeth L. Travis, PhD, Kathryn A. Mason, MSC, *The Cancer Bulletin*, vol. 44, No. 2, pp. 105–110, 1992.

INSTRUMENT FOR CATHETERIZATION

BACKGROUND OF THE INVENTION

In its simplest and earliest form, an instrument for catheterization was a tubular object used to drain noxious material (e.g. pus) from the body. The instrument had a proximal end, generally sharp, to allow penetration of tissue or of a body structure, a tubular shaft with a lumen, and an open distal end to allow drainage and introduction of other substances and devices. This instrument has evolved to a plethora of devices (e.g. needles, catheters of different types, cannulae, and biopsy tools, etc.) for catheterization of structures. Each of these has its own specific use(s), method of insertion, problems and complications.

Catheterization of a blood vessel will be used as an illustration. Catheters for blood vessels were initially developed for insertion into peripheral vessels, those which the practitioner could see and/or feel, e.g. on the dorsum of the hand or along the arm. With advances in medicine, it became necessary to catheterize larger blood vessels, many of which were neither visible nor palpable. This required a change in the procedure of catheterization. Several special-purpose catheters and insertion kits (described hereinafter) have become available for the diagnosis and treatment of medical problems. However, problems still exist during and after catheterization. It is one object of this invention to correct these problems.

There is no catheterization system available which is universal, i.e.:
has a universal procedural method;
can be used to catheterize almost all structures, regardless of the site in/on the body;
can be used both endoscopically and on the surface of the body;
can be used for diagnosis and treatment in all parts of the body using the same procedure.

It is a further object of this invention to be comprehensive, efficient and to fill this void.

This invention rectifies old problems and eliminates some of the newer ones (e.g. risk of AIDS by transmission of the HIV virus from patient to practitioner or vice-versa). Moreover, the invention described here is a universal system. It is also a discriminatory system because it allows a system of treatment that is less toxic to the patient, hence more humane. This system requires fewer hospitalizations and is therefore less expensive. It is more efficient in diagnosis and allows appropriate therapy to be initiated during the same procedure. ILLUSTRATION:

At present, catheterization of the subclavian vein requires the following steps:

1) The skin is cleansed with the solution of choice.
2) The anaesthetic is locally infiltrated.
3) The anatomic landmarks are identified again.
4) The vessel is blindly punctured using a needle with attached syringe.
5) "Flash-back" of blood is observed in the syringe.
6) The syringe is detached from needle so that a guide-wire can be introduced through the hub of the needle.
7) The needle is withdrawn, leaving the guide-wire in place.
8) An incision made in skin at the site of the guide-wire in the skin.
9) A dilator is introduced over the guide-wire through skin into the blood vessel. This makes a passage in the tissues so that the catheter can subsequently be introduced with ease.
10) The dilator is threaded back out over the guide-wire.
11) The catheter is threaded over the guide-wire into the blood vessel.
12) The guide-wire is removed, leaving catheter in place.
13) The infusion lines are attached to the ports of the catheter.
14) The catheter secured to the skin.;
15) Dressing is applied. (Dressing changes are done under sterile conditions every 2-3 days depending on the protocol.)

PROBLEMS

Given the state of the art, the following problems can occur during catheterization. These problems have been corrected by the invention herein submitted.

At present, the practitioner is often required to manipulate the syringe and needle while detaching one from the other. This can dislodge the needle tip from the lumen of the blood vessel. When this occurs, it is necessary to re-attach the syringe to the needle and re-enter the lumen of the blood vessel as evidenced by the "flash-back" of blood into the syringe. Besides being time-consuming and frustrating for both the patient and the practitioner, this exposes the patient to the trauma and risks of multiple punctures. The problem is that there is no continued "flash-back" during the insertion of a guide-wire. Hence damage to the blood vessel and/or the adjacent structures with its attendant morbidity and mortality is more frequently observed in such a scenario.

When the syringe is detached from the needle and the hub of the needle is open to the air, there is a potential risk of air embolism. This may be asymptomatic, but can also be fatal.

These problems continue today. U.S. Pat. Nos. 4,935,008, 4,280,503, 4,655,750 and 4,525,157 have attempted to address the problem of passing a guide-wire without leaving the hub of the needle open to air. They are, however, very limited in that:
only one guide-wire or device can be inserted and the device is not universal
continued "flash-back" is not a feature
none of the problems subsequently discussed are addressed.

Blood flows out of the hub of the needle and there is contact between the patient's blood and practitioner/team members. Although gloves are worn by all members of the team, "breaks" in gloves are well known. Hence there is no guarantee of protection against the transmission of communicable disease-causing agents (e.g., HIV, hepatitis, etc.). Moreover, guide-wires that are available are of a length that often require the practitioner to feed part of the said wire outward while trying to thread the catheter. Thus, the practitioner is again in contact with potentially infected material. Transmission of a communicable disease is obviously a concern. (In the invention herein submitted, at NO time is there contact between any open tissue or body fluid of the patient and practitioner. Moreover, no part of the device introduced into the body of a patient is handled directly by the Practitioner.) Use of surgical gloves is routine, but is not a guarantee against contamination. In the invention herein submitted, the patient and practitioner are protected from being contaminated by each other.

Air embolism can also occur with only a guide-wire in place using the traditional method of catheterization. The present invention rectifies this problem.

Many kits have a guide-wire with a "j" tip. This requires a "feeder" or "straightener" to be attached at the hub of the needle so that the "j" tip is straightened temporarily, thus allowing the guide-wire to be inserted through the needle. This can be a troublesome process and the "feeder" becomes unsterile as it falls off the sterile field. In addition, the needle tip can get dislodged from the lumen of the blood vessel. The present invention rectifies the problem.

Another problem frequently encountered during insertion of the guide-wire is that the direction of the bevel of the needle is not known. Hence the wire can travel in a direction other than that desired by the practitioner. This results in inappropriate positioning of the guide-wire and consequently, of the catheter. A second procedure and/or fluoroscopy is then required for the correct placement of the catheter. This requires additional equipment which subjects the patient to radiation and increases the cost of treatment.

The catheter is secured to the skin directly (i.e., there is communication between the blood stream and skin as long as the catheter is in place. This is a continuing source of infection, both local and systemic, which can lead to many problems resulting in continued hospitalization and even death. U.S. Pat. No. 4,327,723 attempts to combat the problem of infection by the use of a Protective Sleeve. However, the source of infection (i.e., skin to catheter/introducer to bloodstream) is still present and infection continues to be a problem. The catheter is inserted through the introducer lumen. This has the following potential problems:

Clot can form around the catheter if the side-port is not being used. Clot is a good medium for bacterial growth. Hence there is a likelihood of infection.

Frequently, dextrose-rich fluids are infused through the side-port and bathe the catheter. This also assists bacterial growth.

The problem of skin to catheter to bloodstream infection has not been successfully addressed at this time regardless of whether an introducer is used or not.

Another problem is that multiple maneuvers and their attendant problems are required to achieve catheterization. U.S. Pat. No. 4,995,866 attempts to reduce the number of maneuvers required by combining the needle and dilator. However, this is "blind instrumentation" and the end of the dilator can easily penetrate the back wall of the vessel resulting in potentially serious problems.

The following problems can occur *after* catheterization and have been corrected by the present invention:

1) Local and systemic infections. (See above)

2) Multiple dressing changes are required with currently available catheterization devices. Infection can be introduced into the patient by the practitioner and vice-versa, despite the use of sterile techniques. Infection, in particular, is of grave concern today because:
   a) There is a large number of immune-compromised patients in the patient population.
   b) The cost of medical care in the treatment of infections and resultant problems is significant and soaring.
   c) Results of attempted treatment of infections in this population are still poor.

Another problem occurring during dressing changes is that catheters are likely to be inadvertently dislodged from an optimal position. Repositioning and sometimes even the insertion of a new catheter is required. In a critically ill patient, this can be disastrous. Clearly, this contributes to increasing health care costs also. U.S. Pat. No. 4,327,723 purports to allow repositioning of the catheter in a sterile environment. However, this is only temporary because the catheter cannot be adequately immobilized in the new position.

Several problems that occur *during and after* catheterization have also been corrected by the present invention.

At present, infusions of incompatible agents must be administered through different ports. U.S. Pat. No. 4,327,723 describes an introducer to be used simultaneously with a pressure-monitoring catheter. This introducer has only one side-port for infusion. Frequently, this is the only avenue for administering medications or fluids while the monitoring catheter (e.g. Swan Ganz) is being positioned. This is clearly a problem. Moreover, it is necessary to have a "designated" port, for example, for concomitant hyperalimentation. This generally requires inserting another catheter or converting a "pressure monitoring" line into a port for this use. Neither of these options is optimal. Venous access is limited and one of the most frustrating situations for the practitioner and patient is to have no more access sites available.

Problems pertaining to the diagnosis of disease using catheterization include inability to diagnose (e.g. insufficient tissue for diagnosis; tissue obtained is not from the diseased area). Multiple procedures are performed unnecessarily, the patient is subjected to repeated trauma and risks and valuable time and money are wasted.

Treatment of many diseases is non-discriminatory (i.e., medications are introduced systemically into the bloodstream so that all parts of the body, whether diseased or not, are exposed to these substances). For example, a large number of agents used in the treatment of cancer are very toxic. The amounts of these medications that are administered are relatively large due to their subsequent dilution in the body. Were these agents administered primarily to target sites, smaller amounts of the therapeutic agents would be required with less toxicity and "healthy" parts of the body would not be damaged. Furthermore, at present, diagnosis and treatment of diseases (e.g., cancer) is not possible during the same procedure.

Discriminatory treatment of diseases is frequently seen with lesions on the surface of the body only. Diseases located within a body cavity often require treatment using "open" surgical procedures (e.g., interstitial radiation) and/or systemic medications. Treating the "target" organ without exposing the rest of the body to the toxic side effects of current agents (e.g., chemotherapy for cancer) is clearly preferable.

This principle has been applied in the past on a limited basis. However, there are still many associated problems.

U.S. Pat. No. 4,192,302 provides a discriminatory method for treatment of liver cancer. A complex shunt is described to isolate the target organ from the rest of the circulation. The shunt treats the blood from the target organ with a chemotherapeutic agent extracorporeally then detoxifies the blood before returning it to the general circulation. This requires hospitalization and a major operation each time treatment is administered. The cost factor is clear, but more important is the fact that the patient is exposed to repeated morbidity and possible mortality and spends valuable time in the hospital away from the family. U.S. Pat. No. 5,069,662 also describes a discriminatory treatment of liver cancer. The method described is virtually identical to that described in U.S. Pat. No. 4,192,302. The only difference is that catheters are inserted fluoroscopically rather than during an open surgical procedure. Consequently, this procedure also requires multiple hospitalizations and exposes the patient to risks every time the procedure is used (e.g., thrombosis of a vessel, bleeding, damage to the blood vessel such as dissection, etc.).

External radiation has its own well-known complications. Interstitial radiation is used but for lesions within a body cavity, an "open" surgical procedure is necessary. For example, U.S. Pat. No. 4,763,671 addresses local hyperthermia and interstitial radiation. However, an open operation is necessary.

To the best of my knowledge, there is no patent, device or system of catheterization that:

1) deals with the critical problem of transmission of communicable diseases from patient to practitioner or vice-versa 2) allows diagnosis and treatment of diseases regardless of the site of the disease during the same procedure 3) is universal 4) is comprehensive 5) allows discriminatory treatment of diseases regardless of site of disease and involves minimal, if any, hospitalization followed by subsequent treatments at home 6) allows repositioning and firm immobilization of a catheter in its new position in a sterile environment 7) allows multiple separate ports for infusions while inserting monitoring catheters or other tools through the same access site 8) corrects important sources of infection 9) allows the practitioner to know the direction of the bevel of the needle at all times 10) allows the practitioner to observe continuous "flash-back" during maneuvers 11) allows the insertion of more than one device at the same site without the risk of air embolism 12) is time and cost efficient (i.e., the process of catheterization should take less than one minute)

13) has a system of immobilization such that catheters cannot be inadvertently displaced or "pulled out". This problem is significant and, in a critical patient, can mean the difference between life and death.

In summary, there is a clear need for a simple device and system of catheterization which is universal, comprehensive and deals with all of the above issues. The device submitted in the application achieves all this. It also introduces discriminatory treatment for the patient, lowers morbidity and mortality, and allows therapeutic options at low cost.

SUMMARY OF THE INVENTION

The present invention provides for a comprehensive universal instrument and a unified methodology for catheterization as already discussed in detail under the BACKGROUND OF THE INVENTION. The problems therein identified have been corrected. The main components of the present invention are:

a needle which is suitably marked with indicia to indicate the beveled edge of the needle even when the needle tip is not visible to the practitioner;

the needles having two or more lumina to allow the simultaneous introduction of several devices at the same puncture site;

a "Y" connector which allows the practitioner to observe continuous "flash-back" in a syringe while allowing the introduction of a guide-wire, catheter, radiation seeds, biopsy instrument or other tools and systems (the hub of the needle is therefore not open to air at any time);

a syringe which allows the practitioner to observe continuous "flash-back", sample and infuse substances;

a guide-wire of sufficient length so that the practitioner does not come into contact with any part of the wire that has already been in the catheterized system (e.g. bloodstream). Often the practitioner inserts the guide-wire into the system then moves it "out" before threading the catheter, thus "touching" potentially contaminated wire;

a dilator which is incorporated over the needle to allow dilation of tissues for easy insertion of subsequent device. This dilator is tapered so that dilation occurs in a progressive manner. In one embodiment, the dilator has a balloon which, on inflation, allows dilation at the discrimination of the practitioner. The dilator has a tabs for easy maneuverability and also has a self-sealing plug or grommet on the proximal side (i.e., the side closer to the practitioner);

a sheath which is incorporated over the dilator. The sheath is substantially shorter than the dilator and has tabs to allow ease of movement and subsequent securing of the sheath to the skin. In a typical embodiment of the instrument, the sheath does not communicate with the catheterized system (e.g., bloodstream;

the sheath has a self-sealing plug or grommet which may incorporate a bactericidal agent on the proximal end of the sheath;

a "shock" sheath which is introduced with or without another catheter through the sheath in emergency situations where multiple ports are required immediately. The shock sheath has multiple lumens for the reasons described in the BACKGROUND OF THE INVENTION;

a protective sleeve which is pre-assembled. This is not the mode of construction today and practitioners are familiar with the frustrating situation where they have omitted the step of its assembly. The sleeve incorporates the entire catheter, including the port limbs and the sheath, leaving only the tabs of the sheath exposed to allow fixation. The sleeve may be in one or two sections and allows repositioning and firm immobilization of the catheter in different positions while maintaining sterility at all times. The sleeve is easily modified for use over a guide-wire or other tool. The catheter is protected at all times. Hence, contamination and catheter damage should be virtually eliminated.

BRIEF DESCRIPTION OF THE DRAWINGS

For a more complete understanding of the present invention and for further advantages thereof, reference is now made to the following DESCRIPTION OF THE PREFERRED EMBODIMENTS taken in conjunction with the accompanying Drawings in which.

DESCRIPTION OF THE PREFERRED EMBODIMENTS

The embodiments presented are for illustrative purposes only and do not, in any way, limit the scope of the invention. In particular, anyone skilled in the art can make numerous modifications using the proposed instrument system and methodology.

Figures 1, 2, 3:
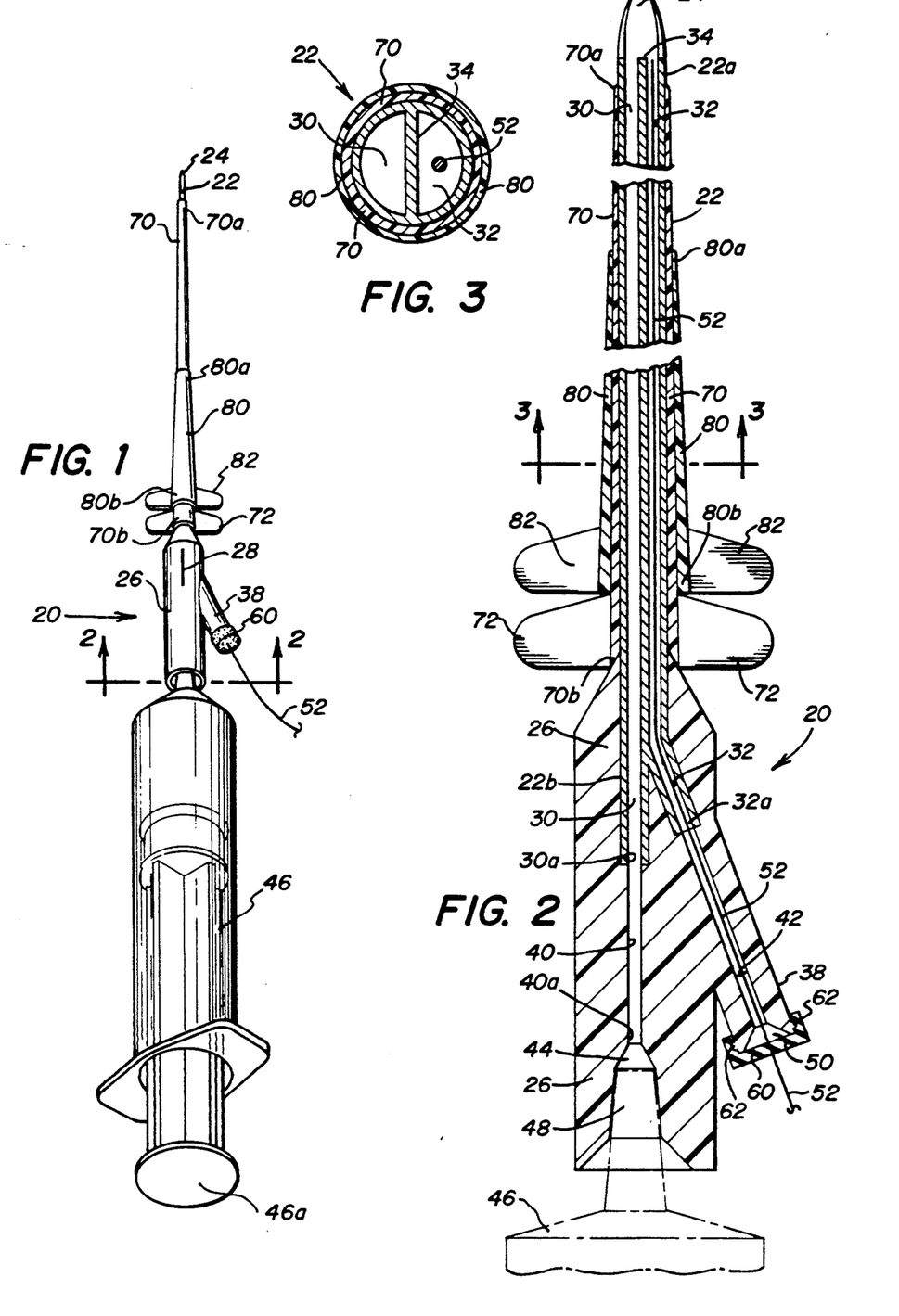
FIG. 1 is a perspective view of the present surgical instrument.
FIG. 2 is a sectional view taken generally along sectional lines 2—2 of FIG. 1.
FIG. 3 is a sectional view taken generally along sectional lines 3—3 of FIG. 2.

Referring simultaneously to FIGS. 1, 2, 3 and 4, the present catheterization surgical instrument is illustrated, and is generally identified by the numeral 20. Surgical instrument 20 includes a needle 22 having a proximal end 22a and a distal or rear end 22b. Needle 22 can be constructed, for example, of stainless steel or similar material and includes a sharpened (preferably beveled) side 24 of needle end 22a. End 22b of needle 22 is interconnected to a hub 26. As illustrated in FIG. 1, hub 26 includes indicia 28 to indicate the direction of beveled side 24 of needle 22. As discussed earlier, indicia 28 assists the practitioner in locating the position of beveled side 24, while needle 22 is inserted into a blood vessel not visible to or palpable by the practitioner (e.g. subclavian vein—a large blood vessel located under the collarbone in the chest).

Needle 22 includes a first longitudinal bore or lumen 30 and a second longitudinal bore or lumen 32. Although lumens 30 and 32 are illustrated in FIG. 2, it will be understood that the present invention can be utilized with any number of lumens (including one) depending upon the number of guide-wires or tools to be inserted through a single puncture site. First lumen 30 and second lumen 32 originate at beveled side 24 in a parallel relationship, with first lumen 30 and second lumen 32 being separated from each other by an interior wall 34 of needle 22. Lumens 30 and 32 are of sufficient internal diameter to allow passage of guide-wires or other tools used in various procedures in the health care field.

Lumen 30 is rectilinear along the entire length of needle 22 and has its terminus 30a at hub 26 of needle 22. Lumen 32 is rectilinear along the substantial longitudinal length of needle 22, with its terminus 32a diverging at an angle from first lumen 30 at hub 26 thereby forming a side arm 38 of needle 22. Hub 26 thereby forms a "Y" connector for use with needle 22.

Where it is desired to use several lumens (i.e., more than two) with the needle 22, additional side arms can be utilized in hub 26 such that additional guide-wires or tools can be inserted through needle 22.

Hub 26 is constructed of plastic or similar material. Hub 26 is concentrically attached to needle 22 at end 22b and side arm 38 in a manner known and used for the attachment of hub casings of single lumen needles. Hub 26 includes an internal bore 40 which is contiguously aligned with first lumen 30. Hub side arm 38 includes an internal bore 42 which is contiguously aligned with second lumen 32.

Bore 40 of hub 26 increases in diameter at bore expansion 44, such that end 40a of bore 40 is adapted to removably engage a standard syringe barrel 46 having a piston 46a and using the inverted frusto-conically shaped aperture 48. Syringe 46 is used for "flash-back", sampling, aspiration and introduction of substances to the catheterized site through lumen 30. Syringe 46 is always in fluid communication with lumen 30 so that there is an uninterrupted communication with the catheterized site. Similarly, bore 42 terminates in an inverted frusto-conically shaped aperture 50 formed in side arm 38 to facilitate the insertion of a guide-wire 52 into bore 42 and second lumen 32 of needle 22.

Bore 42 of side arm 38 is sealingly engaged by a grommet 60. Grommet 60 is constructed of rubber or similar material, and is retained by locking bead 62 of hub 26. Grommet 60 is adapted to be pierced and penetrated by guide-wire 52 (other instrument, tool or device) thereby allowing insertion of guide-wire 52 through grommet 60 and into bore 42 of second lumen 32 while prohibiting the entry of air into or escape of fluid from the catheterized site punctured by beveled end 24 of needle 22.

An important aspect of the present surgical instrument 20 is the use of a dilator 70 having ends 70a and 70b. Dilator 70 is tapered at end 70a to approximately the diameter of end 22a of needle 22 and gradually increases in diameter throughout its length to end 70b. Tapering allows a gradual transition in size to accomplish progressive dilation of the opening in the blood vessel (synonymous with any catheterized site in this presentation) and adjacent tissues with subsequent easy insertion of the catheter.

It is recommended that end 70b of dilator 70 include wings or tabs 72 to allow easy maneuverability of dilator 70 along the guide-wire 52 and along the needle 22 (this latter may be moved out of position depending on the preference of the practitioner). Any standard design for wings or tabs can be used. Dilator 70 fits snugly over needle 22 to ensure that there is no trauma to tissue as a result of a sudden transition in size.

In a preferred embodiment, dilator 70 terminates at end 70a approximately 0.5 to 1.5 cm. from end 22a of needle 22. It is understood that, in general, both the design and length of the dilator can be varied.

An important feature of the present invention is the use of a sheath 80 having ends 80a and 80b. Sheath 80 is circumferentially disposed around dilator 70 and extends from end 70b of dilator 70 to a position between ends 70a and 70b of dilator 70. One embodiment includes wings 82. Other embodiments such as tabs and designs through which sutures are passed can also be used to affix the sheath to the skin 200. Note that, unlike dilator 70, sheath 80 makes no contact whatever with the catheterized site (e.g. bloodstream 206). This corrects two major problems encountered during and after catheterization: infection and air embolism. Infection is virtually eliminated because the sheath 80 is not in direct contact with the bloodstream 206 and the catheter 90, inserted through the sheath 80 into the bloodstream 206, is not in contact with skin 200 at any time. This sheath 80 with its self-sealing grommet 86 prevents air embolism while the guide-wire is in place during the process of catheterization. Moreover, leaving the sheath 80 in place after removal of catheter 90 allows the portion of tract from bloodstream 206 to subcutaneous tissue 202 to heal. Thus, when the sheath 80 is removed, the only remaining tract extends from skin 200 to subcutaneous tissue 202. Hence, the potential for air embolism is virtually eliminated.

Figure 4A:
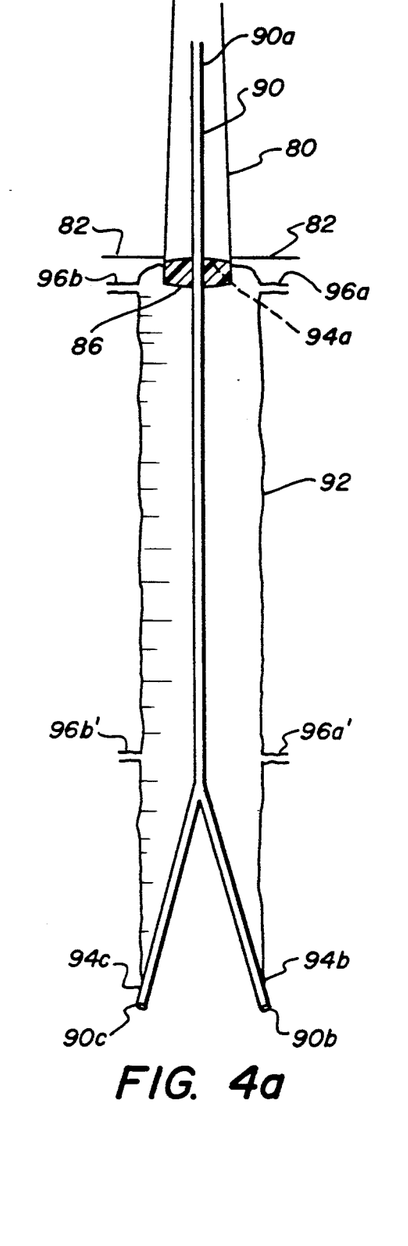
FIG. 4a is a perspective view of the protective sleeve of the present invention.
Figure 4B:
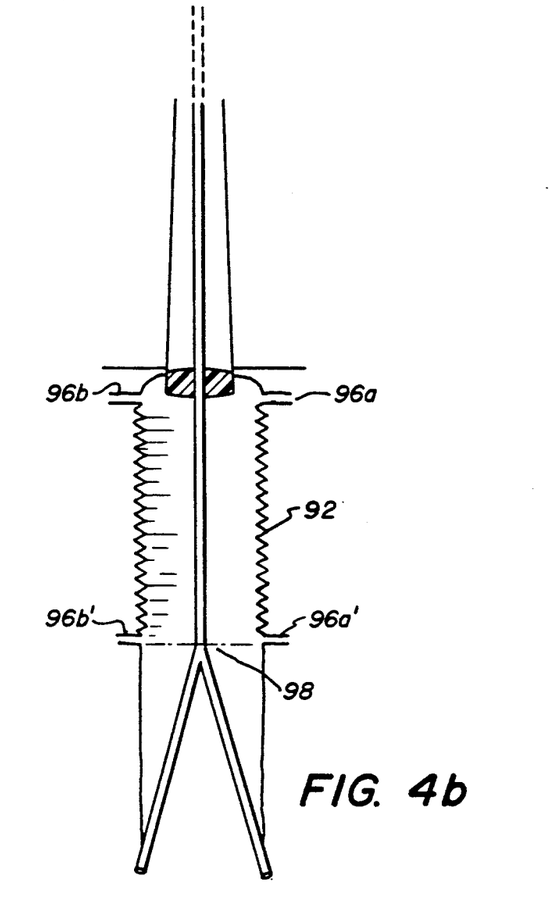
FIG. 4b is a perspective view of the protective sleeve in a collapsed position.

Referring now to FIGS. 4a and 4b, another important component of the submitted invention is a protective sleeve 92 which may be preassembled with a catheter 90. The sheath 80 and its parts as already described includes a self-sealing grommet 86 through which a catheter 90 is passed. The catheter has a proximal end 90a and two ports 90b and 90c. The protective sleeve 92 is, in this instance, made of a synthetic soft material capable of being "accordioned." This sleeve 92 fits circumferentially over the sheath 80 just distal to the tabs 82 of sheath 80 using any sealing mechanism known in the industry (e.g., an "O" ring at location 94a). It is recommended that the space between tabs 82 and location 94a be the least amount consistent with known manufacturing techniques. Protective sleeve 92 is bonded distally to the ends of the catheter ports 90b and 90c at points 94b and 94c leaving only the actual ports (i.e., access sites) exposed. These ports are kept capped and sterile using well-known methods. The protective sleeve 92 covers the entire system outside the patient's skin 200 with the exception of the tabs 82 for fixation of sheath 80. As discussed earlier, these tabs are not in communication with the catheterized area 206 and cannot become a source of infection.

Another novel feature of this invention is the use of multiple tabs. Tabs 96a and 96b on protective sleeve 92 are situated proximally (i.e., nearer sheath 80). Tabs 96a' and 96b' are located distally on protective sleeve 92 (i.e., nearer the ports 90b and 90c of catheter 90). Several embodiments can be used. For example, each tab may have an "eye" allowing the passage of a suture to approximate the "accordioned" length of the protective sleeve 92. Thus, tab 96a would be attached to tab 96a' and tab 96b' to tab 96b'. Any alternative mechanism of attachment may be used also, such as a clip of adjustable length.

FIG. 4b shows the protective sleeve 92 "accordioned" by maneuvering it with the catheter 90. The catheter 90 has been repositioned and immobilized in its new position, maintaining complete sterility. As shown, tab 96a is now closer to tab 96a' and tab 96b is closer to tab 96b'. Another feature that can be easily added is the bonding to or attaching by any other means the protective sleeve 92 to the catheter 90 at site 98. To illustrate further, when used in a body cavity, there is the possibility of the catheter getting kinked. In such a situation, the material of the protective sleeve 92 can be such that the practitioner can mold the form of protective sleeve 92 and decide exactly how he or she wishes the catheter to lie.

Figures 6, 7:
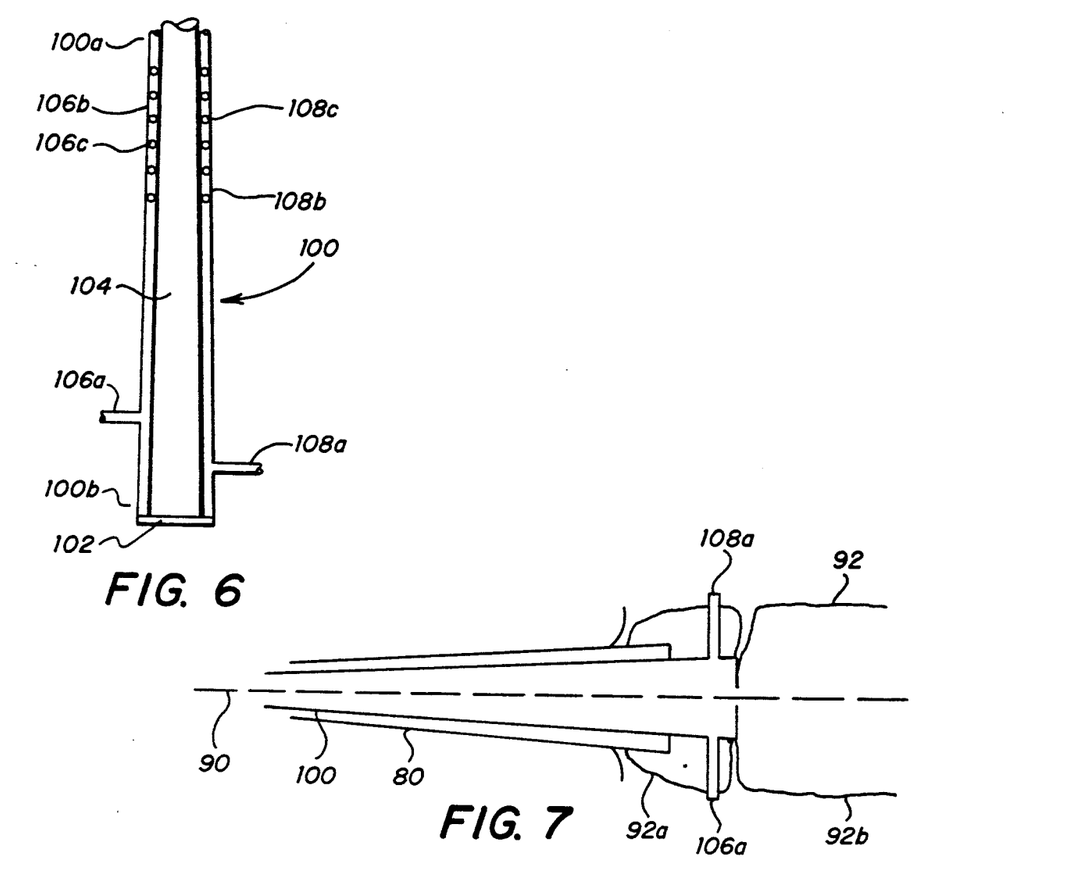
FIG. 6 is a sectional view of the "shock" sheath of the present invention.
FIG. 7 is a side view of an adaptation of the protective sleeve for use with a "shock" sheath and a catheter simultaneously.

It is possible to make this protective sleeve 92 in two parts such that one half is already attached to the sheath 80. This is shown in FIG. 7. Protective sleeve 92a incorporates shock sheath 100 with its sidearms 106a and 108a. Protective sleeve 92b incorporates the catheter 90. However, I believe that the protective sleeve 92 as described earlier is easier for the practitioner to use.

Figure 5:
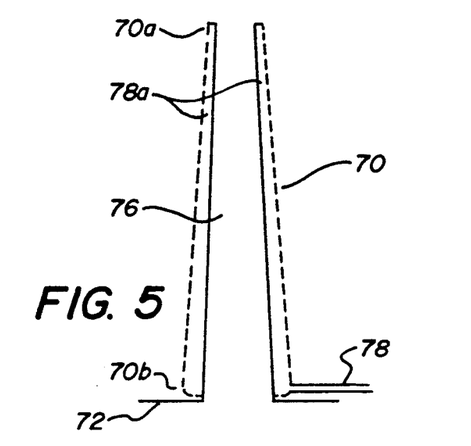
FIG. 5 is an enlarged view of another embodiment of the dilator shown in FIG. 1.

Another preferred embodiment of the dilator 70 is shown in FIG. 5. The dilator 70 has a proximal end 70a and a distal end 70b. Dilator 70 includes a lumen 76. There is a side arm 78 which communicates with lumen 78a, which is circumferentially situated outside lumen 76. The lumen 78a may be dilated with air, water or other substance to an extent determined by the practitioner. It is suggested that this maneuver be performed after the needle 22 has been optimally situated and the guide-wire inserted. This ensures dilation of tissues only when the practitioner is sure that he or she is ready to insert the catheter or tool. In addition, the practitioner can use the same system without regard to the size of the instrument to be inserted.

Yet another important component of the invention is the "shock sheath". FIG. 6 is a sectional view of the shock sheath 100 and shows a proximal end 100a and a distal end 100b. A self-sealing grommet 102 is shown through which a tool (e.g., Swan Ganz catheter) may be passed into the isolated lumen 104 of shock sheath 100. A side arm 106a is shown with its own separate lumen 106b. This lumen 106b has a number of side holes 106c on the outside wall distally to allow the infusions of large volumes of fluids. Similarly, there is a side arm 108a which communicates with its own lumen 108b. Once again, the lumen 108b is not in communication with any other lumen and has multiple holes 108c situated distally. This eliminates the possibility of any cross-contamination from the contents of one lumen to the other. Note that FIG. 6 is only illustrative. If desired, any number of such side arms and lumens may be incorporated. The lumens may be situated longitudinally or circumferentially to each other. When the shock sheath 100 is used, the protective sleeve 92 used will have two parts, 92a and 92b. This device will function according to the principles already described under the description of protective sleeve 92.

FIG. 7 illustrates use of protective sleeve 92, sheath 80, and shock sheath 100. The shock sheath 100 may have tabs which are easily incorporated on the proximal end (i.e., the side towards the practitioner). Antiseptic, bactericidal and other agents may be used to coat or be incorporated into either part of the system or the whole system.

Procedure for Catheterization

The practitioner positions the needle 22 such that the indicia 28 faces the side he or she wishes the guide-wire 52 to exit the needle tip 22a. This is important because it determines the initial course the guide-wire 52 will take in the lumen of the vessel 206 (e.g., the subclavian vein) and dictates the direction of the catheter. Guide-wire 52 pierces grommet 60 and passes into hub 26. The wire exits the needle tip 22a by passing through bore 42 into lumen 32. The practitioner observes continuous flash-back in syringe 46 throughout this procedure.

Figure 8:
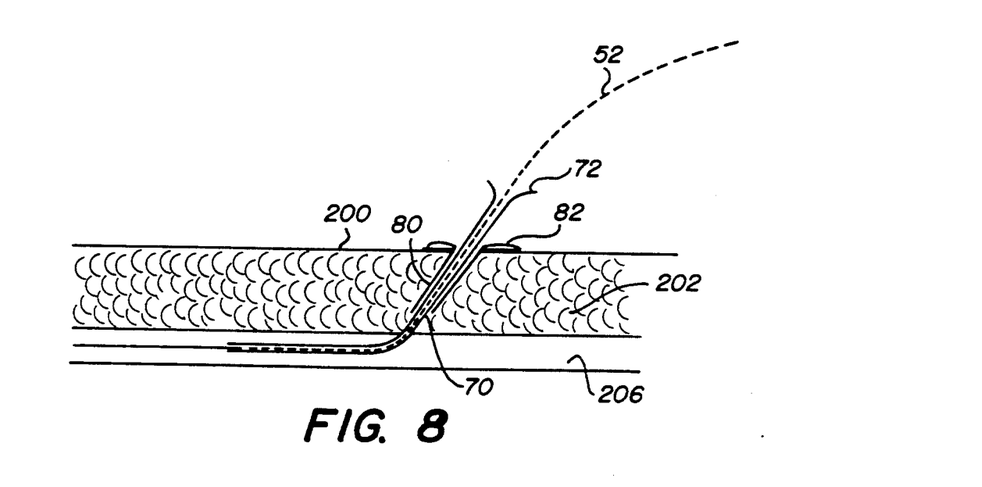
FIG. 8 is a side view of a guide-wire, dilator and sheath in place. (Note that the sheath is secured to the skin and does not communicate with the lumen of the blood vessel.)

The dilator 70 and sheath 80 are maneuvered simultaneously along the guide-wire 52 into blood vessel lumen 206 as the needle 22 with the attached syringe 46 is removed from the puncture site. Tabs 82 of sheath 80 are sutured to the skin 200. FIG. 8 illustrates this.

The dilator 70 is removed and the catheter 90 with the protective sleeve 92 is "threaded" over the guide-wire 52 into the vessel. The protective sleeve 92 is secured at 94a. Tab 96a is attached to tab 96a' and tab 96b to tab 96b'. A small dressing may be applied or a little tincture benzoin sprayed around the area. This is a comprehensive, safe and efficient system. Once the site of catheterization is determined by observing "flash-back", this procedure should take less than one minute to perform. Further care of the catheter and catheterization site is safe (the device cannot be dislodged), infection-free and economical.

Definitive diagnosis of many diseases is obtained by a biopsy. Often the practitioner obtains a sample from the tissue in two steps. The practitioner first aspirates the site to be sure it is not a blood vessel. Once this is ascertained, the lesion is biopsied. Using instrument 20, the lesion is entered with the needle 22 and syringe 46 is used for "flash-back." If no blood is observed, a biopsy forcep is introduced through the side arm 38 of the "Y" connector (as was guide-wire 52 above) and a sample of tissue obtained. There are many different biopsy instruments available to choose from. Certainly, it is easy for one skilled in the field to modify an existing biopsy forcep to fit into instrument 20.

Figure 9:
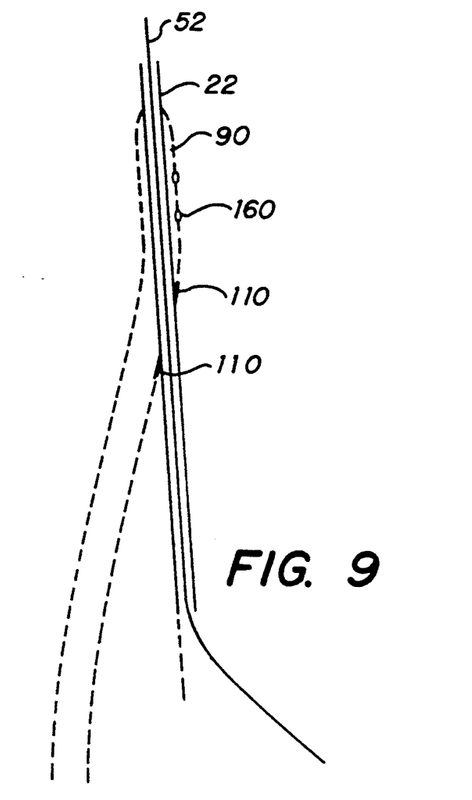
FIG. 9 is a side view of a preferred embodiment of the present invention recommended particularly for use endoscopically and also for discriminatory treatment.

The discriminatory treatment of diseases requires that the agent for treatment be administered either into the blood entering the diseased tissue part or organ, and/or into the diseased tissue. Consider an intracavity cancer in the abdomen or chest. Surgical instrument 20 can be used endoscopically to catheterize the specific blood vessel entering the cancerous organ or even the blood vessel entering the specific part of the organ with cancer. FIG. 9 shows a preferred embodiment. Needle 22 is used to puncture the blood vessel and free "flash-back" ascertained with the syringe 46 as before. Guide-wire 52 is inserted into the lumen of the blood vessel and the catheter 90 is threaded immediately into the lumen of the blood vessel. The "Y" connector and the syringe are not depicted in this figure for clarity. Note that the catheter 90 which has side holes 160 is already in place over the needle 22 at the start of the procedure. This is accomplished by inserting needle 22 through a self-sealing grommet 110 on the side wall of the catheter where grommet 110 can also be a functional side hole of the catheter. It is recommended that the aperture 110 be located close to the distal tip of the catheter. This embodiment is particularly recommended for use endoscopically (e.g. laparoscopically). In this application, the catheter is attached to any of the many available subcutaneous ports and therapeutic agents instilled in the port as desired without any need for subsequent hospitalizations.

Another embodiment includes dilator 70. In this case, it is recommended that the dilator 70 be made of a biodegradable material, so that the dilator can be left in the body at the practitioner's discretion. This procedure requires minimal, if any, hospitalization; is safe, efficient, is discriminatory, and allows treatment at home.

Figure 10:
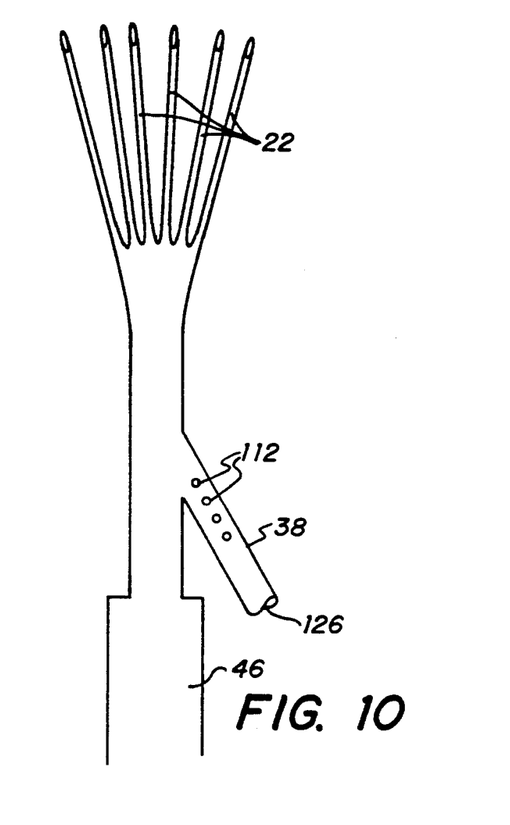
FIG. 10 is a sectional view of yet another embodiment of the invention that can be used for insertion of radioactive seeds.

FIG. 10 illustrates the use of surgical instrument 20 in providing discriminatory treatment by inserting the therapeutic agent directly into the cancer. The lesion is punctured with the needle 22, lack of "flash-back" is observed in syringe 46 and radiation seeds 112 are inserted through the Y connector 38 in lieu of guide-wire 52. This procedure is repeated at different sites on and in the tumor. It is recommended that the needle 22 be marked along its length so that the practitioner varies depth of the needle 22 at different sites within the tumor mass. The insertion of the radiation seeds 112 can be accomplished in several ways and includes (a) maneuvering them along the lumen 32a with a wire or other instrument or (b) using an ejection gun 126 to displace the seeds. If the latter is the preferred method, this invention may be used with multiple needles 22 (instead of just one) as shown in FIG. 10.

Figure 11A:
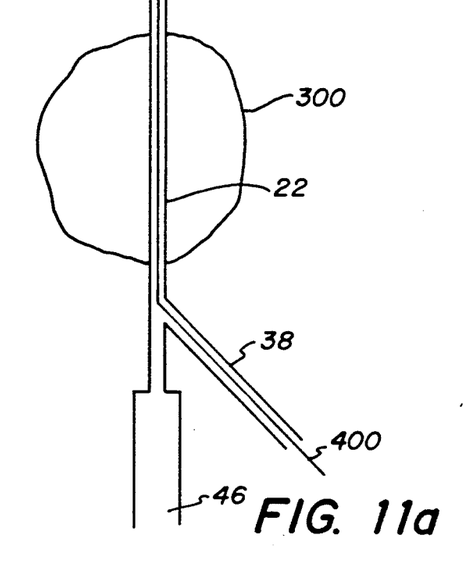
FIG. 11a is a sectional view of an embodiment of the invention that can be used for the insertion of a catheter containing radioactive seeds.
Figure 11B:
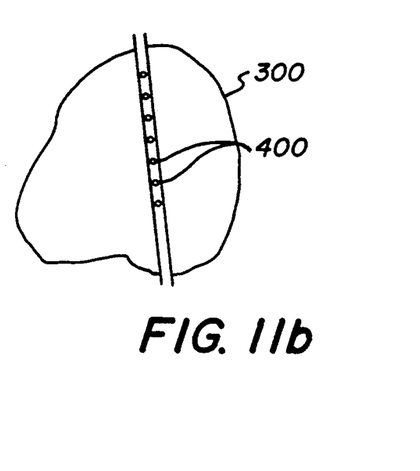
FIG. 11b is a sectional view of the catheter of FIG. 11a in place and extending the entire depth of the tumor. Note that any number of such catheters may be inserted in different planes through the tumor mass.

Referring to FIGS. 11a and 11b, should the practitioner desire to insert a catheter containing radioactive seeds 400 into a tumor 300, it is easily done using this invention. This is done using the same steps as outlined above. Instead of guide-wire 52, a catheter containing radioactive seeds 400 is inserted. Once again, several catheters can be inserted simultaneously.

This invention allows catheterization to be performed anywhere on or in the body (i.e., it is universal); any type of catheterization can be accomplished (i.e, it is uniform); diagnosis and treatment can be performed at the same time using one procedure (i.e., the invention is comprehensive); discriminatory treatment is allowed with minimal or no hospitalization; risk to the patient is reduced; cost to the patient as well as to the health care industry is reduced; the invention improves the quality of life for the patient and should increase his or her length of survival; catheterization is achieved without the multiple problems discussed in the BACKGROUND OF THE INVENTION.

Whereas the present invention has been described with respect to specific embodiments thereof, it will be understood that various changes and modifications will be suggested to one skilled in the art and it is intended to encompass such changes and modifications as fall within the scope of the appended claims. For instance, it is easy for one skilled in the field to modify such catheters using balloons to selectively alter blood flow to the target area.

I claim:

1. A surgical instrument for use with a syringe barrel for drawing blood and inserting guide-wires or other instruments (devices) into a blood vessel, comprising:
    a needle having an elongated shaft, including a hub end and a beveled end for puncturing the blood vessel;
    said needle including a longitudinal lumen extending along the length of said shaft and parallel to said beveled end of said needle;
    a hub attached to said needle, said hub having a first bore in fluid communication with said lumen, said hub being adapted to engage the syringe barrel;
    said hub including a second bore in fluid communication with said lumen for selective insertion of a guide-wire into said lumen; and
    a dilator circumferentially disposed around said needle shaft and extending from said hub to adjacent said beveled end of said needle shaft.

2. The surgical instrument of claim 1 further comprising a sheath circumferentially disposed around said dilator and extending from said hub to a location between said hub and said beveled end of said needle shaft.

3. The surgical instrument of claim 1 wherein said dilator includes first and second ends, said first end being disposed adjacent to said beveled end of said needle and having an outer diameter substantially equal to the outer diameter of said needle, said second end thereof being disposed adjacent to said hub and having an outer diameter greater than the outer diameter of said first end and a tapered portion between said ends.

4. The surgical instrument of claim 3 wherein said second end of said dilator includes means for grasping said dilator.

5. The surgical instrument of claim 4 wherein said grasping means includes tabs.

6. The surgical instrument of claim 2 wherein said sheath includes means for grasping said sheath and disposed adjacent to said hub.

7. The surgical instrument of claim 6 wherein said means for grasping includes tabs.

8. The surgical instrument of claim 1 wherein said hub includes indicia indicating the position of said beveled end of said needle.

9. The surgical instrument of claim 1 wherein said dilator has a self-sealing grommet.

10. The surgical instrument of claim 1 wherein said sheath has a self-sealing grommet.

11. The surgical instrument of claim 1 further comprises:
 a Y connector attached to the hub of said needle which incorporates the aforementioned lumen; and
 said Y connector having one or more lumens and a self-sealing grommet.

12. The surgical instrument of claim 1 wherein said needle includes indicia indicating the position of said beveled end of said needle.

13. A surgical instrument comprising:
 a needle having an elongated shaft, including a hub end and a sharp end beveled in a direction toward a side of said needle;
 said needle having one or more longitudinal lumens extending along the length of said shaft of said needle and parallel to said beveled side of said needle;
 a dilator circumferentially disposed around said needle shaft and extending from said hub to said beveled end of said needle such that the dilator is shorter than the total length of said needle shaft and said dilator has a tapered end towards said beveled end of said needle;
 said dilator end adjacent to the beveled end of said needle having an outer diameter substantially equal to the outer diameter of said needle;
 said dilator including tabs adjacent said hub of said needle;
 a sheath circumferentially disposed around said dilator wherein said sheath is substantially shorter than said dilator with a tapered end towards said beveled end of said needle;
 said sheath including tabs adjacent said hub of said needle; and
 a protective sleeve for enclosing said sheath.

14. The surgical instrument of claim 13, wherein said dilator includes a wall having a lumen circumferentially disposed around said needle such that said wall can be filled with air or fluid for controlling the diameter of said dilator.

15. The surgical instrument of claim 13 and further including a shock sheath disposed within said sheath and including multiple ports for receipt or withdrawal of fluids.

16. The surgical instrument of claim 13 wherein protective sleeve has a variable length.

17. The surgical instrument of claim 13 and further including:
 a catheter circumferentially disposed around said needle.

18. The surgical instrument of claim 13 wherein said dilator is biodegradable.

19. The surgical instrument of claim 13 wherein said hub includes indicia indicating the direction of said beveled side of said end of said needle.

20. The surgical instrument of claim 17 wherein said needle is inserted through a self-sealing grommet or side-hole or distal tip of the catheter.

21. The surgical instrument of claim 13 wherein multiple lumens may be incorporated in different components of the system.

22. The surgical instrument of claim 13 wherein said protective sleeve encompasses a catheter or sleeve device used therein.

23. A surgical instrument for use with a syringe barrel for drawing blood and inserting guide-wires or other instruments (devices) into a blood vessel, comprising:
 a needle having an elongated shaft, including a hub end and a beveled end beveled toward a beveled side for puncturing the blood vessel, each of said needle, said hub end and said beveled end having an outer diameter;
 said needle including a longitudinal lumen extending along the length of said elongated shaft and parallel to said beveled side of beveled end of said needle;
 a hub attached to said needle, said hub having a first bore in fluid communication with said lumen, said hub being adapted to engage said syringe barrel;
 said hub including a second bore in fluid communication with said lumen for selective insertion of a guide-wire into said lumen;
 a Y connector attached to said hub of said needle which incorporates said lumen, said Y connector having at least one additional lumen and a self-sealing grommet;
 a dilator circumferentially disposed around said needle shaft and extending from said hub to adjacent said beveled end of said needle shaft, said dilator having a self-sealing grommet; and
 a sheath circumferentially disposed around said dilator, extending from said hub to a location between said hub and said beveled end of said needle shaft, said sheath having a self-sealing grommet.

24. The surgical instrument of claim 23 wherein said dilator includes first and second ends, said first end being disposed adjacent said beveled end of said needle and having an outer diameter substantially equal to the outer diameter of said needle, said second end of said dilator being disposed adjacent said hub and having an outer diameter greater than the outer diameter of said first end and a tapered portion between said first and second ends of said dilator.

25. The surgical instrument of claim 24 wherein said second end of said dilator includes a means for grasping said dilator.

26. The surgical instrument of claim 25 wherein said means for grasping said dilator includes tabs.

27. The surgical instrument of claim 23 wherein said sheath includes means for grasping said sheath, said sheath grasping means disposed adjacent to said hub.

28. The surgical instrument of claim 27 wherein said means for grasping said sheath includes tabs.

29. The surgical instrument of claim 23 wherein said beveled end of said needle has a beveled side and said hub includes indicia indicating the position of said beveled side of said beveled end of said needle.

30. The surgical instrument of claim 23 wherein said beveled end of said end of said needle has a beveled side and said needle includes indicia indicating the position of said beveled side of said beveled side of said needle.

31. A surgical instrument comprising:
   a needle having an elongated shaft, including a hub end and a sharp beveled end;
   said needle having one or more longitudinal lumens extending along the length of said shaft of said needle and parallel to said beveled end of said needle;
   a dilator circumferentially disposed around said needle shaft and extending from said hub to said beveled end of said needle such that the dilator is shorter than the total length of said needle shaft and said dilator has a tapered end towards said beveled end of said needle;
   said dilator end adjacent to said beveled end of said needle having an outer diameter substantially equal to the outer diameter of said needle;
   said dilator including tabs adjacent said hub of said needle;
   a sheath circumferentially disposed around said dilator wherein said sheath is substantially shorter than said dilator with a tapered end towards said beveled end of said needle;
   said sheath including tabs adjacent said hub of said needle; and
   a protective sleeve for enclosing said sheath and for encompassing a catheter or other device used herein.

32. The surgical instrument of claim 31, wherein said dilator includes a wall having a lumen circumferentially disposed around said needle such that said wall can be filled with air or fluid for controlling the diameter of said dilator, where said dilator may be tapered.

33. The surgical instrument of claim 31 and further including a shock sheath disposed within said sheath and including multiple ports for infusion or withdrawal of fluids.

34. The surgical instrument of claim 31 wherein said protective sleeve has a variable length and form.

35. The surgical instrument of claim 31 and further including:
   a catheter circumferentially disposed around said needle.

36. The surgical instrument of claim 31 wherein said dilator is biodegradable.

37. The surgical instrument of claim 31 wherein said hub includes indicia indicating the position of said beveled end of said needle.

38. The surgical instrument of claim 31 wherein said needle is inserted through a self-sealing grommet in said catheter.

39. The surgical instrument of claim 31 wherein multiple lumens may be incorporated in different components of said surgical instrument.

* * * * *

UNITED STATES PATENT AND TRADEMARK OFFICE
CERTIFICATE OF CORRECTION

PATENT NO. : 5,257,979

DATED : NOVEMBER 2, 1993

INVENTOR(S) : RAVINDAR JAGPAL

It is certified that error appears in the above-identified patent and that said Letters Patent is hereby corrected as shown below:

Column 1, line 3, after the title of the invention, insert the following:

---Technical Field of the Invention:

The present invention relates to surgical instruments and, in particular, to a universal instrument for the introduction of a catheter, cannula or tool into any part of the body. The instrument allows diagnosis and treatment of disease using the same procedure. The instrument includes a needle, syringe, Y chamber, guidewire, dilator, sheath, shock sheath and protective sleeve. Methodology for discriminatory treatment of disease using embodiments of said instrument is described.

DEFINITIONS AND TERMINOLOGY

The following terms used herein shall be defined as:

Universal:

- may be used anywhere in or on the body;

- may be used for diagnosis or treatment of disease;

- may be used for temporary or permanent devices;

- may be used by health care personnel in different fields of health care.

Comprehensive:

- all necessary components are included in the instrument.

UNITED STATES PATENT AND TRADEMARK OFFICE
CERTIFICATE OF CORRECTION

PATENT NO. : 5,257,979

DATED : NOVEMBER 2, 1993

INVENTOR(S) : RAVINDAR JAGPAL

It is certified that error appears in the above-identified patent and that said Letters Patent is hereby corrected as shown below:

Discriminatory:  --

- treatment is focused on the diseased part(s) of the body so that systemic toxicity is markedly reduced (*e.g.*, chemotherapeutic agents, external radiation, etc.).

Disease:

- all altered states of body and mind;

- all processes leading to altered states of body and/or mind.

Catheter:

- includes tool, instrument, cannula or other device.

Diagnosis (includes, but is not limited to):

- angiograms of all types;

- obtaining specimens for study (*e.g.*, blood, pleural fluid, tissues, etc.);

- obtaining pressure measurements (e.g., Swan Ganz catheter);

- injection of radioactive and other materials.

Treatment (includes, but is not restricted to):

- drainage (*i.e.*, pus, urine, other fluids and substances);

- infusion (*i.e.*, fluids, chemicals and other substances);

UNITED STATES PATENT AND TRADEMARK OFFICE
CERTIFICATE OF CORRECTION

PATENT NO. : 5,257,979
DATED : NOVEMBER 2, 1993
INVENTOR(S) : RAVINDAR JAGPAL

It is certified that error appears in the above-identified patent and that said Letters Patent is hereby corrected as shown below:

-- radioactive seeds and other materials.

In this application, the term "blood vessel" is used as an illustration only and is not by way of limitation for the scope of the present invention.---

Column 6, line 33, insert ---)--- following "bloodstream".

Column 9, line 52, replace "96" (first occurrence) with ---96---. (inventor's mistake)

Signed and Sealed this

Eleventh Day of June, 1996

Attest:

BRUCE LEHMAN

*Attesting Officer*      *Commissioner of Patents and Trademarks*